United States Patent [19]

Faber et al.

[11] Patent Number: 5,326,387
[45] Date of Patent: Jul. 5, 1994

[54] SURFACE PROTECTANT COMPOSITION

[75] Inventors: Robert D. Faber, Grand Rapids; Steven J. Brouwer, Hudsonville, both of Mich.

[73] Assignee: Amway Corporation, Ada, Mich.

[21] Appl. No.: 925,970

[22] Filed: Aug. 5, 1992

[51] Int. Cl.$^5$ .............................................. C09G 1/14
[52] U.S. Cl. .................... 106/3; 106/287.11; 106/287.12; 106/287.13; 106/287.14
[58] Field of Search ............ 106/3, 2, 287.11, 287.12, 106/287.13, 287.14

[56] References Cited

U.S. PATENT DOCUMENTS

| | | | |
|---|---|---|---|
| 2,645,588 | 7/1953 | Barry | 106/287.13 |
| 2,770,631 | 11/1956 | Merker | 106/3 |
| 2,831,008 | 4/1958 | Knopf et al. | 106/3 |
| 3,471,541 | 10/1969 | Morehouse | 106/3 |
| 3,544,498 | 12/1970 | Holdstock et al. | 106/3 |
| 3,801,572 | 4/1974 | Berger | 106/3 |
| 3,890,269 | 6/1975 | Martin | 260/46.5 |
| 3,960,575 | 6/1976 | Martin | 106/10 |
| 4,218,250 | 8/1980 | Kasprzak | 106/3 |
| 4,246,029 | 1/1981 | Sanders, Jr. | 106/3 |
| 4,247,330 | 1/1981 | Sanders, Jr. | 106/3 |
| 4,273,584 | 6/1981 | D'Angelo et al. | 106/3 |
| 4,366,001 | 12/1982 | Ona et al. | 106/287.12 |
| 4,459,382 | 7/1984 | Ona et al. | 106/287.11 |
| 4,462,828 | 7/1984 | Otsuki | 106/3 |
| 4,467,068 | 8/1984 | Maruyama et al. | 524/731 |
| 4,509,981 | 4/1985 | Sanders, Jr. et al. | 106/3 |
| 4,612,055 | 9/1986 | Manis et al. | 106/287.14 |
| 4,785,067 | 11/1988 | Brumbill | 106/8 |
| 4,997,478 | 3/1991 | Gordon | 106/3 |
| 5,017,222 | 5/1991 | Cifuentes et al. | 106/3 |
| 5,043,012 | 8/1991 | Shinohara et al. | 106/10 |
| 5,057,151 | 10/1991 | Schuster et al. | 106/287.12 |
| 5,092,922 | 3/1992 | Kuwata et al. | 106/3 |

FOREIGN PATENT DOCUMENTS

| | | |
|---|---|---|
| 0494648A2 | 7/1992 | European Pat. Off. . |
| 2036051A | 6/1980 | United Kingdom . |

OTHER PUBLICATIONS (Article) Information About Volatile Silicone Fluids, Dow Corning, 1988, 6 pages.
(Article) Masil 123 Amino-Functional Silicone, Technical Quality Bulletin, Mazer, 1989, 6 pages.

*Primary Examiner*—Helene Klemanski
*Attorney, Agent, or Firm*—Willian Brinks Hofer Gilson & Lione

[57] ABSTRACT

An automobile surface protectant composition containing volatile silicone which when applied to a wet surface displaces water and imparts gloss and water repellency. Preferably, the composition includes a volatile silicone fluid, an amino-functional silicone fluid, and an organopolysiloxane fluid.

11 Claims, No Drawings

5,326,387

SURFACE PROTECTANT COMPOSITION

BACKGROUND OF THE INVENTION

This invention relates to a liquid surface protectant composition used to impart a durable high gloss finish, as well as water repellency, to surfaces such as painted automobile surfaces, vinyl, rubber, and leather goods. The invention also relates to a method of using the composition.

Surface protectant compositions, polishes, and waxes containing silicone compounds are known in the art. For example, high gloss protective coatings for automobile finishes have traditionally involved the application of a wax to the dry exterior surface followed by buffing the applied wax. A wide variety of products formulated with hydrocarbon or vegetable-based waxes, silicone polymers, and various additives are commercially available. Nearly all waxes, however, are difficult to apply uniformly and require extensive buffing to provide a high gloss or shine. In addition, these coatings are not well suited for application to rubber and vinyl surfaces. Moreover, the surface typically must be dried prior to applying the wax.

Protective coatings which can be applied onto the rubber, vinyl, or leather surfaces of an automobile are also known. Typically, these protective coatings are applied using an aerosol or pump spray applicator. These protective coatings are generally emulsions, either an oil-in-water or a water-in-oil type, which require substantial wiping to achieve uniform gloss. Unfortunately, these coatings typically are not suitable for the painted surfaces of the automobile.

Consequently, there exists a need for a surface protectant composition that can be applied to a variety of surfaces yet is easy to apply, is self-leveling over the surface and provides a high gloss. More importantly, there exists a need for a surface protectant that can be applied to the surface when the surface is wet to impart a gloss and water beading performance onto the surface.

SUMMARY OF THE INVENTION

Briefly stated, the invention is directed to a quick-leveling liquid surface protectant composition together with a method of imparting a protective coating. The composition includes from about 10 to about 99.9 percent by weight of a volatile silicone fluid, from about 0.1 to about 10 percent by weight of a cross-linkable silicone fluid, and, optionally from 1 to about 50% of organopolysiloxane fluids.

The protectant composition can be applied to the surface of, for example, an automobile having a wet surface to aid in displacing the water and to impart a glossy appearance and water repellency.

In a preferred embodiment, the composition includes from about 65 to about 85 percent by weight of a volatile silicone fluid consisting of one or more polydimethylcyclosiloxane fluids having the general formula $[(CH_3)_2SiO]_x$ where x has a value from three to eight; from about 0.1 to about 5 percent by weight of a cross-linkable silicone fluid consisting of an aminofunctional polysiloxane and from about 1 to about 30 percent by weight of one or more tri-methyl end capped organopolysiloxane fluids.

It is noted that, unless otherwise stated, all percentages given in this specification and the appended claims refer to percentages by weight of the total composition.

It is further noted that, unless otherwise stated, all viscosities refer to the viscosity measured by ASTM D445 at 25° C.

The present composition can be easily and evenly applied, leveling more efficiently than available products. More importantly, in contrast to other well known types of polishes and protective coatings, the present protectant composition can be applied to surfaces that are wet. When the composition is applied to a wet surface it displaces the water present on the surface and imparts onto the surface a glossy appearance and water beading performance. Thus, the present invention also comprehends a method of displacing water to impart a glossy appearance and water repellency onto surfaces including, but not limited to, painted metal, vinyl, leather, rubber, masonry, concrete, glass, ceramic, fiberglass, and wood surfaces. Because this invention is particularly useful on automobile surfaces, it will be described herein by reference to automobile surfaces. Such description, however, is not intended to limit the scope of the invention.

DETAILED DESCRIPTION OF THE PREFERRED EMBODIMENTS

In a first embodiment of the invention a liquid surface protectant composition is provided which includes a combination of a volatile silicone fluid and an aminofunctional silicone fluid with, optionally, one or more organopolysiloxane fluids. Thus, the composition comprises a combination of a major amount of a volatile silicone fluid and a minor amount of an amino-functional silicone fluid with an optional amount of one or more organopolysiloxane fluids.

Volatile silicone fluids generally are low viscosity silicone fluids with an appreciable vapor pressure at ambient temperatures. Generally, the volatile silicone fluids useful in the present invention have a viscosity of less than about 10 cSt. at 25° C., preferably less than about 5 cSt. at 25° C. Preferred volatile silicone fluids include the polydimethylcyclosiloxanes.

Polydimethylcyclosiloxane fluids useful in the present invention can be defined by the general formula $[(CH_3)_2SiO]_x$ where x has a value from three to eight. Generally, the polydimethylcyclosiloxane fluid useful in the present invention is a mixture of one or more of the various species represented by the above formula. The commercial polydimethylcyclosiloxanes are mixtures of the various species represented by the above formula and are considered within the scope of the present invention.

The preferred polydimethylcyclosiloxane fluids for use in this invention are those where octamethylcyclotetrasiloxane, decamethylcyclopentasiloxane, and dodecamethylcyclohexasiloxane (i.e. where x is from 4 to 6) predominate. The fluids where decamethylcyclopentasiloxane and dodecamethylcyclohexasiloxane predominate are particularly preferred. In accordance with the most preferred embodiment, those volatile silicone fluids manufactured by Dow Corning Corporation under the trade name Dow Corning® 245 fluid and 345 fluid are used. It is believed that Dow Corning 245 fluid consists of about 95% decamethylcyclopentasiloxane and 345 fluid consists of about 75% decamethylcyclopentasiloxane and about 25% dodecamethylcyclohexasiloxane.

The polydimethylcyclosiloxane fluid constitutes a major amount of the protectant composition. In particular, the polydimethylcyclosiloxane fluid constitutes from about 10 to about 99.9 percent by weight of the protectant composition, preferably from about 55 to about 99.9 percent, more preferably from about 65 to about 85 percent. In accordance with the most preferred embodiment, the polydimethylcyclosiloxane constitutes about 79% of the protectant composition.

The protectant composition also includes a minor amount of a cross-linkable silicone fluid, preferably an amino-functional polysiloxane, which aids in the water displacement and water beading performance of the composition. In addition, amino-functional silicone fluids are thought to be useful in protectant compositions because it is believed that they attach to the anionic surfaces of, for example, an automobile and at the same time, when water vapor is present, they cross-link to provide a longer lasting gloss and a more durable protective film. Accordingly, the type and amount of amino-functional silicone fluid useful in the present invention can be dictated by, among other things, the desired resulting properties of the protectant composition as well as its compatibility with the other ingredients. In particular, those amino-functional silicone fluids that cloud the composition when incorporated with the other ingredients are not desired.

Preferably, the amino-functional silicone fluids include, but are not limited to, those polysiloxanes with the general formula:

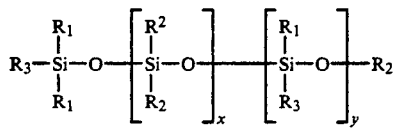

wherein x+y ranges from 2 to 20, preferably wherein x ranges from 2 to about 20 and y is 1. $R_1$ is an oxy radical, e.g. hydroxy, methoxy, ethoxy, and the like. Preferably, $R_1$ is selected from the group consisting of hydroxy, alkoxy, alkenoxy, phenoxy, and mixtures thereof. More preferably, $R_1$ is selected from the group consisting of alkoxy having up to about 8 carbon atoms and mixtures thereof. In accordance with the most preferred embodiment, $R_1$ is selected from the group consisting of methoxy, ethoxy, and mixtures thereof.

$R_2$ may be an alkyl radical, e.g. methyl, ethyl, propyl, butyl, octyl, dodecyl and octadecyl; aryl radical, e.g., phenyl, diphenyl and naphthyl radical; alkenyl radical, e.g., vinyl and alkyl radical; cycloalkyl radical, e.g., cyclobutyl, cyclopentyl, and cyclohexyl; alkaryl radical, e.g., tolyl, xylyl, ethylphenyl; aralkyl radical, e.g. alpha-phenylethyl, beta-phenylethyl and alpha-phenylbutyl and the like. Preferably, $R_2$ is selected from the group consisting of alkyl, aryl, and mixtures thereof. More preferably $R_2$ is selected from the group consisting of alkyl having up to about 18 carbon atoms, phenyl, and mixtures thereof. Particularly preferred is where $R_2$ is selected from the group consisting of methyl, ethyl, phenyl, and mixtures thereof.

$R_3$ is an amine radical, e.g. primary, secondary, and tertiary amines as well as diamines. Preferably, $R_3$ is selected from the group consisting of alkylamines, alkyldiamines and mixtures thereof. More preferably, $R_3$ is selected from the group consisting of alkylamines having up to about 8 carbon atoms, alkyldiamines having up to about 16 carbon atoms, and mixtures thereof. In accordance with the most preferred embodiment, an amino-functional silicone manufactured by PPG Mazer Chemicals under the trade name Masil® 123 is used. This product is a proprietary amino-functional silicone fluid containing both aminofunctionality and alkoxyfunctionality.

The amount of amino-functional polysiloxane incorporated in the protectant composition can vary. Generally speaking, however, at least about 0.1 percent is usually necessary to obtain reasonable water displacement and beading performance. It is preferred to use up to about 10 percent with from about 0.1to about 5 percent being more preferred. In accordance with the most preferred embodiment, about 1 percent of the amino-functional silicone fluid is incorporated in the protectant composition.

As noted above, the protectant composition of the present invention may optionally contain one or more organopolysiloxanes. In the preferred embodiment organopolysiloxanes are included in the composition to provide consumer desired characteristics. In particular, medium viscosity (i.e., greater than about 350 cSt.) organopolysiloxanes can be included to provide gloss characteristics to the composition. In addition, low viscosity (i.e., about 50 to about 350 cSt.) organopolysiloxanes can be included to provide some leveling and drag reducing attributes to the composition. Accordingly, the present composition preferably includes one or more organopolysiloxane fluids to provide these attributes.

The low to medium viscosity organopolysiloxane fluids useful in the present invention may be either linear or branched chained siloxanes having a viscosity from about 50 to about 10,000 cSt. at 25° C. In particular, those organopolysiloxanes with a viscosity from about 50 to about 1,000 cSt. at 25° C. are preferred. Of course, it is possible to blend organopolysiloxane fluids having different viscosities to form a fluid having the desired viscosity range. Alternatively, it is possible to use one or more organopolysiloxane fluids, each having a different viscosity, in the protectant composition to produce the desired end-product characteristics.

Organopolysilozanes useful in the present composition are those compounds having the general formula:

$$\text{R}-\underset{\underset{\text{R}}{|}}{\overset{\overset{\text{R}}{|}}{\text{SiO}}}-\left[\underset{\underset{\text{R}}{|}}{\overset{\overset{\text{R}}{|}}{\text{SiO}}}\right]_x-\underset{\underset{\text{R}}{|}}{\overset{\overset{\text{R}}{|}}{\text{Si}}}-\text{R}$$

wherein the R's may be the same or different and can be alkyl radicals, e.g. methyl, ethyl, propyl, butyl, octyl, dodecyl and octadecyl; aryl radicals, e.g., phenyl, diphenyl and naphthyl radicals; alkenyl radicals, e.g., vinyl and alkyl radicals; cycloalkyl radicals, e.g., cyclobutyl, cyclopentyl, and cyclohexyl; alkaryl radicals, e.g., tolyl, xylyl, ethylphenyl; aralykyl radicals, e.g. alpha-phenylethyl, and x has a numerical value from about 40 to about 800, providing a viscosity of 50 to 10,000 cSt.

Those polysiloxanes where R is selected from the group consisting of aryl, those alkyl radicals having up to about 30 carbon atoms, and mixtures thereof are preferred, especially those where the polysiloxane is tri-methyl end capped. The polysiloxanes where R is selected from the group consisting of phenyl, those alkyl radicals having up to about 15 carbon atoms, and mixtures thereof are more preferred especially those where the polysiloxane is tri-methyl end capped: More particularly, a combination of two low viscosity (i.e., about 50 to about 350 cSt.) tri-methyl end capped polydimethylsiloxanes or a low viscosity (i.e., about 50 to about 350 cSt.) and a medium viscosity (i.e., about 350 to about 10,000 cSt.) tri-methyl end capped polydimethylsiloxane are preferred. A combination of a tri-methyl end capped polydimethylsiloxane having a viscosity of about 50 cSt. at 25° C. and a tri-methyl end capped polydimethylsiloxane having a viscosity of about 350 cSt. at 25° C. is most preferred.

The amount and type of organopolysiloxane fluid useful in the present invention will depend upon the desired characteristics sought for the protectant composition and the compatibility with the other ingredients of the composition. The amount of organopolysiloxane included in the present invention, however, must not be so great that the other desired attributes of water displacement and beading are detrimentally affected.

Accordingly, where the organopolysiloxane fluid is included it can be included in the protectant composition in amounts from about 1 to about 50 percent. When the organopolysiloxane fluid is incorporated into the composition, the maximum amount of volatile silicone fluid present will be about 98.9 percent. Preferably, the organopolysiloxane is included in an amount from about 1 to about 30 percent, more preferably from about 1 to about 20 percent. In accordance with the most preferred embodiment, the organopolysiloxane fluid is included in an amount of about 20 percent and is a 1:1 mixture of a tri-methyl end capped polydimethylsiloxane having a viscosity of about 50 cSt. and a tri-methyl end capped polydimethylsiloxane having a viscosity of about 350 cSt.

The composition can be prepared by thoroughly mixing with slight agitation each of the components. Preferably, the composition is prepared by the following steps: charge the desired amount of the volatile silicone fluid to a mix vessel, add the organopolysiloxane fluid (or if more than one, add each) to the mix vessel with slight agitation, then add the cross-linkable silicone fluid to the mix vessel with slight agitation and continue to agitate at ambient temperature until all the ingredients are thoroughly mixed.

In a more preferred embodiment of the invention, the liquid protectant composition consists essentially of a volatile silicone fluid, a crosslinkable silicone fluid, and an organopolysiloxane fluid with each of the fluids as described above present in the composition at the levels also described above. For example, in this more preferred embodiment, the liquid protectant composition consists essentially of from about 10 to about 98.9 percent of a volatile silicone fluid consisting of the polydimethylcyclo. siloxane fluids described above, from about 0.1 to about 10 percent of a cross-linkable silicone fluid consisting of the amino-functional silicone fluids described above, and from about 1 to about 50 percent of the organopolysiloxanes described above.

In another embodiment of the invention, it is contemplated that the liquid protectant composition described above may be incorporated into an oil-in water emulsion wherein the emulsifier would be selected so as to not negate the benefits of the invention.

The composition of the present invention can be used effectively on many different surfaces to provide water displacement and beading and to impart a gloss to those surfaces. For example, it can be used effectively on the painted body of an automobile. It is to be understood, however, that the protectant composition is also effective when applied to rubber, vinyl, and other surfaces. Typically, the protectant is applied to the surface to be protected and thereafter the surface is buffed or rubbed with a suitable fiber-containing material including, but not limited to, a rag, cloth, cheese cloth, rumple cloth, flannel, cotton diaper cloth, non-woven fabrics and the like, to impart a glossy appearance and to provide water repellency.

Uniquely, the present protectant composition can be effectively used while the surface to be protected is still wet. Thus, when, for example, an automobile is to be protected, the automobile need not be dried prior to applying the composition of the present invention. A fiber containing material which has been wetted with the present composition can be rubbed over the surface of the automobile which will displace the water present on the surface and further impart upon buffing a remaining glossy appearance which exhibits beading of water when water contacts the surface to which the protectant has been applied.

The composition can also be applied to the surface to be protected by the use of an aerosol, preferably a non-polar aerosol, by a pump spray, or by wetting a sponge or cloth and then applying the sponge or cloth to the surface. Of course, other means of applying the composition are contemplated. Preferably, as the porosity of the surface increases, it is desirable to apply the composition directly to the surface using a spray or an aerosol. On the other hand, where the surface is relatively non-porous, such as on a painted automobile surface, it is desirable to first apply the protectant composition to an applicator such as a sponge, cloth, and the like and then apply the treated applicator to the surface. Thereafter, it is preferred that the surface, if it is painted, be rubbed or buffed to impart an even, glossy appearance and provide water repellency.

EXAMPLES

The following examples are given to illustrate, but not limit, the invention. Table 1 shows six compositions that were prepared and tested for two desired attributes of the invention, water displacement upon application and water beading after buffing. These compositions incorporate various levels of the critical elements of the invention. The test was performed generally in conformance with ASTM D3836 in the following manner. A dry terry cloth applicator was wetted with the protectant composition and then applied uniformly and evenly over an approximately three square foot area of a painted automobile surface which had been previously wetted with deionized water. The water displacement performance of each composition was visually evaluated and rated by experts. After the application of the composition, the surface was buffed. The water beading performance of each composition was visually evaluated and rated by experts by misting water onto the treated surface.

The following results were observed: For water displacement, Composition 1 was better than Composition 2 which was better than Composition 3 which was about the same as Composition 4 and 5 which were better than Composition 6. For water beading after buffing, Composition 1 was better than Composition 2 which was better than Composition 3 which was better than Composition 5 which was about the same as Composition 6 which was better than Composition 4.

Table 2 shows six compositions, each within the scope of the present invention, that were prepared and evaluated for water displacement upon application and water beading after buffing. The testing was performed as described above.

The following was observed: For water displacement, Composition 8 was better than Composition 7 which was about equal to Composition 10 which was better than Composition 9 which was better than Composition 11 which was about the same as Composition 12. For water beading, Composition 10 was about the 1 same as Composition 8 which was better than Composition 9 which was about the same as Composition 7 which was better than Composition 11 which was about the same as Composition 12. Even though some of the above compositions were found to perform better than others, it is to be noted that each of the Compositions 7-12 were effective.

TABLE 1

| Component | Composition (Weight Percent) | | | | | |
|---|---|---|---|---|---|---|
| | 1 | 2 | 3 | 4 | 5 | 6 |
| Polydimethylcyclo-siloxane* | 99.0 | 99.5 | 99.9 | 100.0 | — | — |
| Odorless Mineral Spirits | — | — | — | — | 99.0 | — |
| Ethanol | — | — | — | — | — | 99.0 |
| Amino-functional Polysiloxane** | 1.0 | 0.5 | 0.1 | — | 1.0 | 1.0 |

*Dow Corning 345 Fluid
**PPG/Mazer Masil ® 123

TABLE 2

| Component | Composition (Weight Percent) | | | | | |
|---|---|---|---|---|---|---|
| | 7 | 8 | 9 | 10 | 11 | 12 |
| Polydimethylcyclo-siloxane* | 79.0 | 89.0 | 79.0 | 89.0 | 79.0 | 79.0 |
| Amino-functional Polysiloxane** | 1.0 | 1.0 | 1.0 | 1.0 | 0.1 | 0.1 |
| Polydimethylsiloxane (350 cSt.) | 20.0 | 10.0 | — | — | 20.0 | — |
| Polydimethylsiloxane (50 cSt.) | — | — | 20.0 | 10.0 | — | 20.0 |

*Dow Corning 345 Fluid
**PPG/Mazer Masil ® 123

It should be understood that a wide range of changes and modifications can be made to the embodiments described above. It is therefore intended that the foregoing description illustrates rather than limits this invention, and that it is the following claims, including all equivalents, which define this invention.

We claim:

1. A nonaqueous surface protectant composition comprising:
   a. from about 10 to about 99.9 percent by weight of a volatile silicone fluid;
   b. from about 0.1 to about 10 percent by weight of a cross-linkable silicone fluid; and,
   c. optionally, from about 1 to about 50 percent by weight of an organopolysiloxane fluid.

2. The composition of claim 1 wherein the volatile silicone fluid is selected from the group consisting of polydimethylcyclosiloxanes having the general formula $[(CH_3)_2SiO]_3$ wherein x has a value from 3 to 8, and mixtures thereof.

3. The composition of claim 1 wherein the crosslinkable silicone fluid is a polysiloxane of the general formula

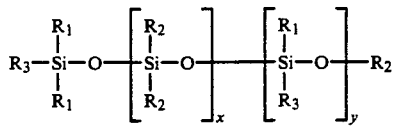

in which $R_1$ is an oxy radical, $R_2$ is selected from the group consisting of alkyl, aryl, and mixtures thereof, $R_3$ is selected from the group consisting of an alkylamine radical, an alkyldiamine radical, and mixtures thereof, and x+y ranges from 2 to 20.

4. The composition of claim 1 wherein the organopolysiloxane is a polysiloxane of the general formula

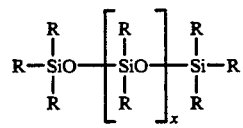

wherein R is selected from the group consisting of alkyl radicals having up to about 30 carbon atoms, aryl, and mixtures thereof, and x has a numerical value from about 40 to about 800, providing a viscosity of 50 to 10,000 cSt. at 25° C.

5. A nonaqueous automobile surface protectant composition comprising:
   a. from about 10 to about 98.9 percent by weight of a volatile silicone fluid selected from the group consisting of polydimethylcyclosiloxanes having the formula $[(CH_3)_2SiO]_x$ wherein x has a value from 3 to 8, and mixtures thereof;
   b. from about 0.1 to about 10 percent by weight of an amino-functional silicone fluid, wherein the amino-functional silicone fluid is a polyxiloxane of the general formula

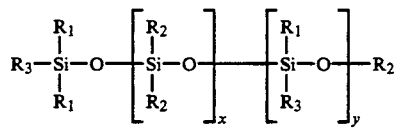

in which $R_1$ is an oxy radical, $R_2$ is selected from the group consisting of alkyl, aryl, and mixtures thereof, $R_3$ is selected from the group consisting of an alkylamine radical, an alkyldiamine radical, and mixtures thereof, x is from 2 to about 20, y is 1; and
   c. from about 1 to about 50 percent by weight of an organopolysiloxane fluid, wherein the organopolysiloxane is a polysiloxane of the general formula

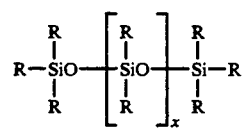

wherein R is selected from the group consisting of alkyl radicals having up to about 30 carbon atoms, aryl, and mixtures thereof, and x has a numerical value from about 40 to about 800, providing a viscosity of 50 to 10,000 cSt. at 25° C.

6. A nonaqueous automobile surface protectant composition comprising:

a. from about 65 to about 85 percent by weight of a volatile silicone fluid;
b. from about 0.1 to about 5 percent by weight of an amino-functional silicone fluid; and,
c. from 1 to about 30 percent by weight of an organopolysioxane fluid.

7. The composition of claim 6 wherein the volatile silicone fluid is selected from the group consisting of polydimethylcycosiloxanes having the formula $[(CH_3)_2SiO]_x$ wherein x has a value from 3 to 8, and mixtures thereof.

8. The composition of claim 6 wherein the amino-functional silicone fluid is a polysiloxane of the general formula

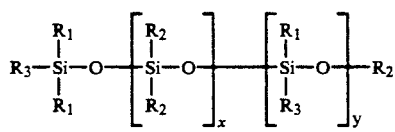

in which $R_1$ is an oxy radical, $R_2$ is selected from the group consisting of alkyl, aryl, and mixtures thereof, $R_3$ is selected from the group consisting of an alkylamine radical, and alkyldiamine radical, and mixtures thereof, x ranges from 2 to about 20 and y is 1.

9. The composition of claim 6 wherein the organopolysiloxane is a polysiloxane of the general formula

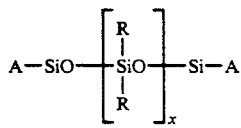

in which A is $(CH_3)_3$, R is selected from the group consisting of alkyl radicals having up to about 30 carbon atoms, aryl, and mixtures thereof, and x has a numerical value from about 40 to about 800, providing a viscosity of 50 to 10,000 cSt. at 25° C.

10. A nonaqueous automobile surface protectant composition comprising:
a. about 79 percent by weight of a volatile silicone fluid selected from the group consisting of decamethylcyclopentasiloxane, dodecamethylcyclohexasiloxane, and mixtures thereof.
b. about 1 percent by weight of an amino-functional silicone fluid, wherein the amino-functional silicone fluid is a polysiloxane of the general formula

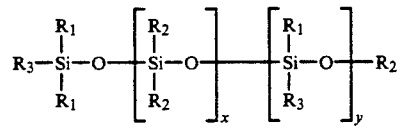

in which $R_1$ is methoxy, $R_2$ is selected from the group consisting of methyl, phenyl, and mixtures thereof, and $R_3$ is selected from the group consisting of alkylamine, alkyldiamine, and mixtures thereof, x is from 2 to about 20 and y is 1; and,
c. about 10 percent by weight of a tri-methyl end capped polydimethylsiloxane having a viscosity of about 50 cSt. at 25° C.; and
d. about 10 percent by weight of a tri-methyl end capped polydimethylsioxane having a viscosity of about 350 cSt. at 25° C.

11. A method of displacing water from a painted, rubber, or vinyl surface of an automobile to thereby impart a glossy appearance and water repellency to the surface comprising:
a. applying a quick-leveling protectant composition to the surface, the composition comprising:
  i. from about 10 to about 98.9 percent by weight of a volatile silicone fluid;
  ii. from about 0.1 to about 10 percent by weight of an amino-functional silicone fluid; and,
  iii. from 1 to about 50% of an organopolysiloxane fluid; and
b. rubbing the resulting film-covered surface as needed with a suitable fiber-containing material.

* * * * *